(12) United States Patent
Zhang et al.

(10) Patent No.: US 12,085,540 B1
(45) Date of Patent: Sep. 10, 2024

(54) ROCK TRUE-TRIAXIAL TESTING SYSTEM BASED ON COMPUTERIZED TOMOGRAPHY (CT) SCANNING

(71) Applicant: INSTITUTE OF GEOLOGY AND GEOPHYSICS, CHINESE ACADEMY OF SCIENCES, Beijing (CN)

(72) Inventors: Zhaobin Zhang, Beijing (CN); Tianqiao Mao, Beijing (CN); Xiao Li, Beijing (CN); Shouding Li, Beijing (CN); Jianming He, Beijing (CN); Guanfang Li, Beijing (CN); Bo Zheng, Beijing (CN); Yanzhi Hu, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/668,176

(22) Filed: May 19, 2024

(30) Foreign Application Priority Data

Jul. 5, 2023 (CN) .......................... 202310814017.X

(51) Int. Cl.
*G01N 3/12* (2006.01)
*G01N 3/02* (2006.01)
(Continued)

(52) U.S. Cl.
CPC ................. *G01N 3/12* (2013.01); *G01N 3/02* (2013.01); *G01N 23/046* (2013.01); *G01N 33/24* (2013.01);
(Continued)

(58) Field of Classification Search
CPC .......... G01N 3/12; G01N 3/02; G01N 23/046; G01N 33/24; G01N 2203/0019; G01N 2203/0256; G01N 2203/0641
See application file for complete search history.

(56) References Cited

U.S. PATENT DOCUMENTS

| 10,948,431 | B1 * | 3/2021 | Zheng ..................... G01N 33/24 |
| 11,048,002 | B1 * | 6/2021 | Mao ........................ G06T 17/05 |
| 2022/0196527 | A1 | 6/2022 | Zhang et al. |

FOREIGN PATENT DOCUMENTS

| CN | 105181471 A | 12/2015 |
| CN | 110542614 A | 12/2019 |

(Continued)

*Primary Examiner* — Jonathan M Dunlap
(74) *Attorney, Agent, or Firm* — Bayramoglu Law Offices LLC

(57) ABSTRACT

A rock true-triaxial testing system based on computerized tomography (CT) scanning aims to solve problems in the prior art, that is, the rigidity of the frame in the testing system is insufficient; high-pressure lines, wires, and signal lines are entangled when rotating; and the reaction frame and loading actuators obstruct the ray. The rock true-triaxial testing system includes a true-triaxial loading system and a high-energy accelerator-based CT scanning system, where the high-energy accelerator-based CT scanning system is located inside the true-triaxial loading system, and the high-energy accelerator-based CT scanning system is configured to image an internal structure of a cubic rock sample and continuously apply a stress to the cubic rock sample through a plurality of piston extension rods in the true-triaxial loading system. The rock true-triaxial testing system reduces radiation attenuation, and ensures imaging quality and a stable and smooth loading process.

6 Claims, 5 Drawing Sheets

(51) Int. Cl.
*G01N 23/046* (2018.01)
*G01N 33/24* (2006.01)

(52) U.S. Cl.
CPC ............... *G01N 2203/0019* (2013.01); *G01N 2203/0256* (2013.01); *G01N 2203/0641* (2013.01)

(56) References Cited

FOREIGN PATENT DOCUMENTS

| | | | | |
|---|---|---|---|---|
| CN | 111157557 A | * | 5/2020 | ........... G01N 23/046 |
| CN | 111238973 A | | 6/2020 | |
| CN | 111766369 A | * | 10/2020 | ............. G01N 33/24 |
| CN | 112014228 A | | 12/2020 | |
| CN | 112051287 A | * | 12/2020 | ........... G01N 23/046 |
| CN | 112067458 A | | 12/2020 | |
| CN | 112504832 A | | 3/2021 | |
| CN | 112903470 A | * | 6/2021 | ......... G01N 15/0806 |

* cited by examiner

ROCK TRUE-TRIAXIAL TESTING SYSTEM BASED ON COMPUTERIZED TOMOGRAPHY (CT) SCANNING

CROSS REFERENCE TO THE RELATED APPLICATIONS

This application is based upon and claims priority to Chinese Patent Application No. 202310814017.X, filed on Jul. 5, 2023, the entire contents of which are incorporated herein by reference.

TECHNICAL FIELD

The present disclosure belongs to the field of rock mechanics tests and devices for rock mechanics tests, and in particular relates to a rock true-triaxial testing system and method based on computerized tomography (CT) scanning.

BACKGROUND

The evolution process of rock fracture under the action of three-dimensional geostress, temperature, and fluid is a frontier scientific issue in the field of earth science. Deep understanding of the formation, expansion, penetration, and instability of microcracks in rocks is crucial for major engineering construction, efficient development of energy resources, and understanding and evaluation of deep fault activation in the earth. Therefore, opening the "black box" of rock fracture, acquiring the evolution process of rock fracture, and accurately predicting rock fracture and its location have important engineering and scientific significance.

A real-time computerized tomography (CT) scanning system can be combined with a rock true-triaxial testing system to cause the dynamic evolution study of rock fracture under the action of three-dimensional geostress, temperature, and fluid to be transparent and intuitive. Many scholars worldwide have conducted relevant research on this topic and have achieved a number of results. However, the CT scan-based rock true-triaxial testing system has some shortcomings.

Chinese Patent Application 202010911726.6 provides a rigid-flexible true-triaxial grouting-seepage coupled testing device and method based on CT scanning. The testing device includes a first principal stress loading system, a second principal stress loading system, a third principal stress flexible loading system, a rigid pad assembly system, a base part, a grouting system, a grout discharge system, and a data acquisition system. The testing device can perform a true-triaxial grouting-seepage coupled test on a sample fracture, and acquire the variation law of the fractal dimension of the fracture, the permeability coefficient, and the grout diffusion and filling during the grouting-seepage coupled test through a CT scan image to study the coupling mechanism between the grout and rock during the grout seepage process. However, the relevant system does not provide a solution to the 360-degree rotation needed for CT scanning and the resulting entanglement problems of grouting lines, hydraulic lines for loading systems, and signal lines, etc.

Chinese Patent Application 201510577392.2 provides a rock true-triaxial testing system and method using a real-time CT scanning system. The testing system includes a true-triaxial pressure cell, a true-triaxial host frame, a loading device, and a CT scan device. The true-triaxial host frame and components in the scanning area are made of a carbon fiber to reduce CT radiation attenuation. However, this creates a new problem, that is, the rigidity of the carbon fiber is insufficient. As a result, when a hard rock test is conducted, the frame will deform greatly to accumulate elastic potential energy. When the rock reaches peak strength, the accumulated elastic potential energy in the frame will be instantly released, resulting in direct damage to the rock sample and preventing the acquisition of a complete stress-strain curve of the rock (this is also why the maximum loading force in this disclosure is only 100 KN). In addition, this disclosure still does not provide a solution to the problem of line entanglement.

Chinese Patent Application 202010973324.9 provides a rock true-triaxial testing system and method using microscopic online CT scanning. The testing system includes a true-triaxial tester, an automatic turntable, a CT radiation source, a CT detector, a control cabinet, and a console. The true-triaxial tester is directly placed above the automatic turntable, and the automatic turntable drives the true-triaxial tester to rotate. The air and hydraulic lines are all flexible lines. The air and hydraulic lines must be organized in advance before the start of a test to prevent them from getting tangled, and the entanglement of the air and hydraulic lines must be observed during the test. This increases the workload and risk level in the test. Because of certain radiation of CT, personnel cannot stay at the test site and can only operate remotely. Besides, the hydraulic lines need to have a certain pressure-bearing capacity. During loading, even flexible hydraulic lines are adopted, they also can become hard due to high-pressure hydraulic oil, which increases the difficulty of rotating the line. In addition, in this disclosure, the rock sample is surrounded by a reaction frame and blocked by a plurality of stress actuators, which cause severe radiation attenuation, resulting in failure to image or extremely poor imaging quality.

Chinese Patent Application 202011400744.4 provides a true-triaxial testing device and method based on real-time CT scanning for a high-pressure hard rock fracture process. This testing device can study the high-pressure hard rock fracture process, but it does not provide a technical solution to the entanglement problems of loading actuators, confining pressure lines, and pressure sensor signal lines.

In view of the above, the present disclosure provides a rock true-triaxial testing system based on CT scanning.

SUMMARY

The present disclosure aims to solve the above problems in the prior art. That is, in the prior art, the rigidity of the frame in the testing system is insufficient; high-pressure lines, wires, and signal lines are entangled when rotating; and the reaction frame and loading actuators obstruct the ray. The present disclosure provides a rock true-triaxial testing system based on computerized tomography (CT) scanning, including a true-triaxial loading system and a high-energy accelerator-based CT scanning system, where
   the true-triaxial loading system is fixed to a ground and configured to apply a true-triaxial stress to a cubic rock sample; and
   the high-energy accelerator-based CT scanning system is located inside the true-triaxial loading system, and the high-energy accelerator-based CT scanning system is configured to image an internal structure of the cubic rock sample and rotate around the cubic rock sample.

In some preferred implementations, the true-triaxial loading system includes a true-triaxial reaction frame, first loading pads, pressure sensors, the cubic rock sample, a first-axis loading system, a second-axis loading system, and a third-axis loading system;

the first-axis loading system includes first loading cylinders, first piston extension rods, first piston guide frames, and first displacement sensors;

the true-triaxial reaction frame is fixed to the ground and the first loading cylinder; a piston rod of the first loading cylinder is fixed to one end of the pressure sensor, and the other end of the pressure sensor is fixed to the first piston extension rod; the first piston extension rod passes through the high-energy accelerator-based CT scanning system and is fixed to the first loading pad; the first loading pad is configured to squeeze the cubic rock sample; the cubic rock sample is connected to the high-energy accelerator-based CT scanning system; the first piston extension rod is located inside the first piston guide frame; and the first piston guide frame is fixed to the true-triaxial reaction frame;

the first displacement sensor is fixed to the first loading cylinder and configured to measure a displacement distance of the first piston extension rod;

two first loading cylinders, two first piston extension rods, two first piston guide frames, two first displacement sensors, two first loading pads, and two pressure sensors are symmetrically arranged along a center line of the true-triaxial reaction frame; and the second-axis loading system and the third-axis loading system are fixed to the true-triaxial reaction frame.

In some preferred implementations, the second-axis loading system includes second loading cylinders, second piston extension rods, second piston guide frames, and second displacement sensors;

the true-triaxial reaction frame is fixed to the second loading cylinder; a piston rod of the second loading cylinder is fixed to one end of the pressure sensor, and the other end of the pressure sensor is fixed to the second piston extension rod; the second piston extension rod passes through the high-energy accelerator-based CT scanning system and is fixed to the first loading pad; the first loading pad is configured to squeeze the cubic rock sample; the second piston extension rod is located inside the second piston guide frame; and the second piston guide frame is fixed to the true-triaxial reaction frame;

the second displacement sensor is fixed to the second loading cylinder and configured to measure a displacement distance of the second piston extension rod; and two second loading cylinders, two second piston extension rods, two second piston guide frames, two second displacement sensors, two first loading pads, and two pressure sensors are symmetrically arranged along the center line of the true-triaxial reaction frame.

In some preferred implementations, the third-axis loading system includes a third loading cylinder, a third displacement sensor, and a second loading pad;

the true-triaxial reaction frame is fixed to the third loading cylinder; a piston rod of the third loading cylinder is fixed to one end of the pressure sensor, and the other end of the pressure sensor is fixed to the second loading pad; and the second loading pad is configured to squeeze the cubic rock sample; and the third displacement sensor is fixed to the third loading cylinder and configured to measure a displacement distance of the second loading pad.

In some preferred implementations, the high-energy accelerator-based CT scanning system includes a high-energy accelerator-based CT support base, a turntable stator, a rotating tow, a turntable rotor, a detector bracket, a detector, a detector lifting system, a radiation source bracket, a radiation source, and a radiation source lifting system;

a lower surface of the high-energy accelerator-based CT support base is connected to the true-triaxial reaction frame, and an upper surface of the high-energy accelerator-based CT support base is connected to the cubic rock sample and the turntable stator; and the turntable stator is connected to the turntable rotor through a bearing;

the turntable rotor is fixed to the detector bracket; the detector bracket is fixed to the detector lifting system; the detector lifting system is fixed to the detector; and the detector is configured to image the internal structure of the cubic rock sample;

the turntable rotor is fixed to the radiation source bracket; the radiation source bracket is fixed to the radiation source lifting system; the radiation source lifting system is fixed to the radiation source; and the radiation source is configured to emit an X-ray to the cubic rock sample; and the cubic rock sample is connected to the high-energy accelerator-based CT support base; an end of the rotating tow is fixed to the turntable rotor, and the rotating tow is configured to coil around an outer circumference of the turntable stator; and the rotating tow is configured to pull a CT line of the high-energy accelerator-based CT scanning system.

In some preferred implementations, the high-energy accelerator-based CT support base includes a base connecting plate, CT support bosses, and a lower reaction pad;

a lower surface of the base connecting plate is fixed to the true-triaxial reaction frame, and an upper surface of the base connecting plate is fixed to the plurality of CT support bosses; and the plurality of CT support bosses are fixed to the turntable stator; and an upper surface of the base connecting plate is fixed to a lower surface of the lower reaction pad, and an upper surface of the lower reaction pad is fixed to the cubic rock sample.

In some preferred implementations, the system further includes an oil source power system; and the oil source power system is fixed to the ground and configured to provide a power source for the true-triaxial loading system.

In some preferred implementations, the system further includes a comprehensive control system; and the comprehensive control system is fixed to the ground and configured to implement loading control and signal acquisition of the true-triaxial loading system, as well as control and acquisition of photoelectric and control signals of the high-energy accelerator-based CT scanning system.

In some preferred implementations, the lower reaction pad is configured to provide a supporting reaction force for the cubic rock sample.

In some preferred implementations, the first loading pads are made of titanium alloy or aviation aluminum alloy.

The present disclosure has following beneficial effects:

The present disclosure uses a plurality of piston extension rods to keep the loading device out of the field of view of the CT scan, thereby reducing radiation attenuation and ensuring imaging quality. The present disclosure uses a plurality of piston guide frames to limit the shaking of the piston extension rods, ensuring a smooth and efficient loading process and effectively solving the problem of radiation obstruction caused by the reaction frame and loading actuators. In addition, the present disclosure uses loading pads made of a low-density alloy, which ensures rigidity and less radiation absorption, thereby improving imaging quality.

BRIEF DESCRIPTION OF THE DRAWINGS

Other features, objectives and advantages of the present disclosure will become more apparent upon reading the detailed description of the non-restrictive embodiments with reference to the following drawings.

DETAILED DESCRIPTION OF THE EMBODIMENTS

Figure 1:
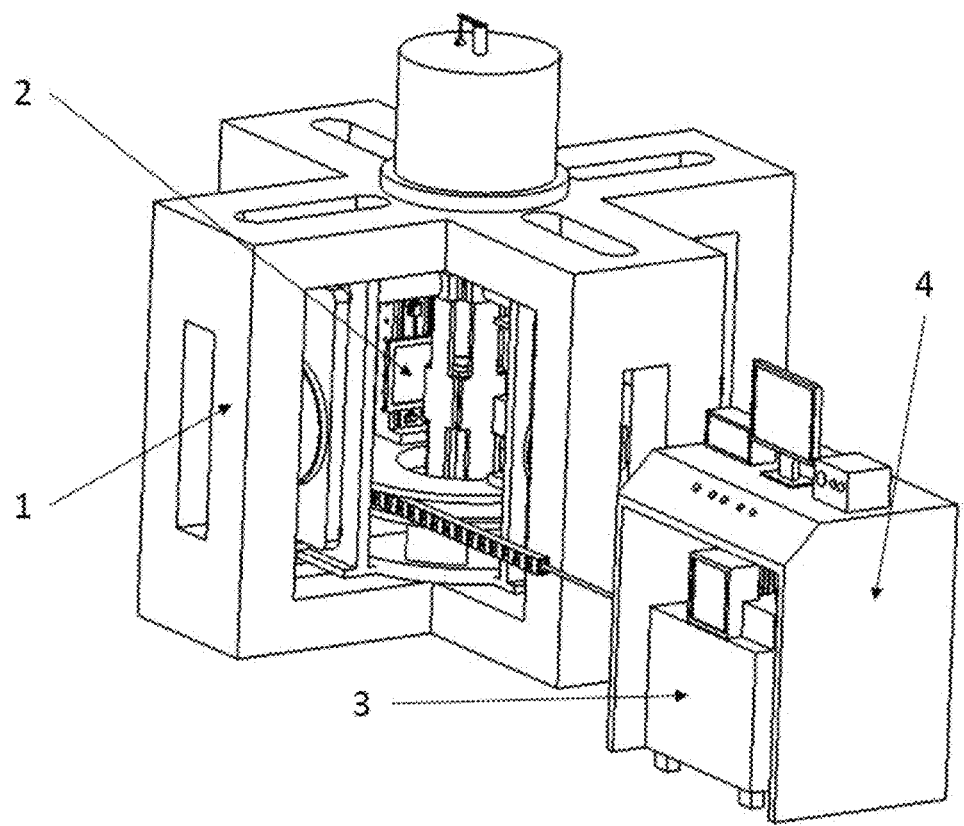
FIG. 1 is an isometric diagram of a rock true-triaxial testing system based on computerized tomography (CT) scanning according to the present disclosure.

The present disclosure will be further described in detail below in conjunction with the drawings and embodiments. It should be understood that the specific embodiments described herein are merely intended to explain the present disclosure, rather than to limit the present disclosure. It should also be noted that, for convenience of description, only the parts related to the present disclosure are shown in the drawings.

It should be noted that the embodiments in the present disclosure and features in the embodiments may be combined with each other in a non-conflicting situation. The present disclosure will be described in detail below with reference to the drawings and embodiments.

Figure 2:
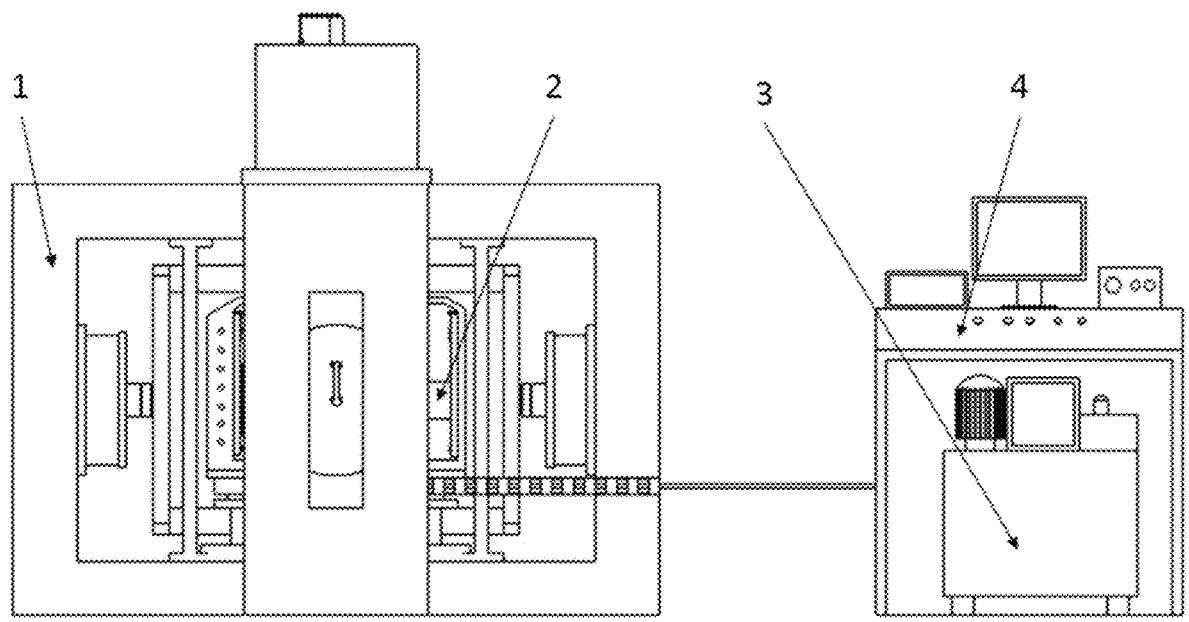
FIG. 2 is a front view of a rock true-triaxial testing system based on CT scanning according to the present disclosure.
Figure 6:
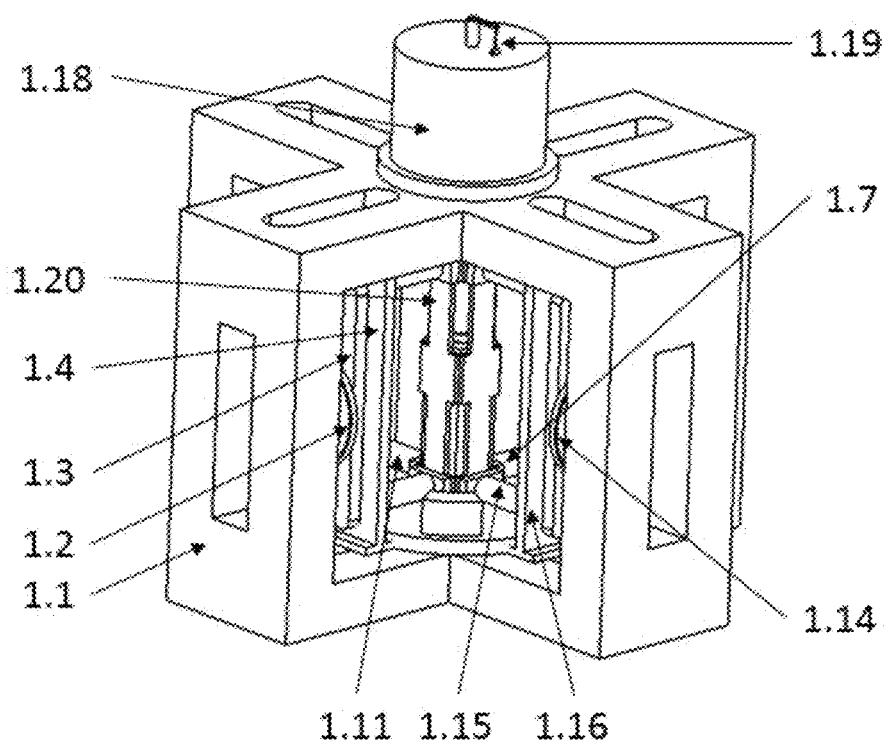
FIG. 6 is an isometric diagram of a true-triaxial loading system of the rock true-triaxial testing system based on CT scanning according to the present disclosure.
Figure 7:
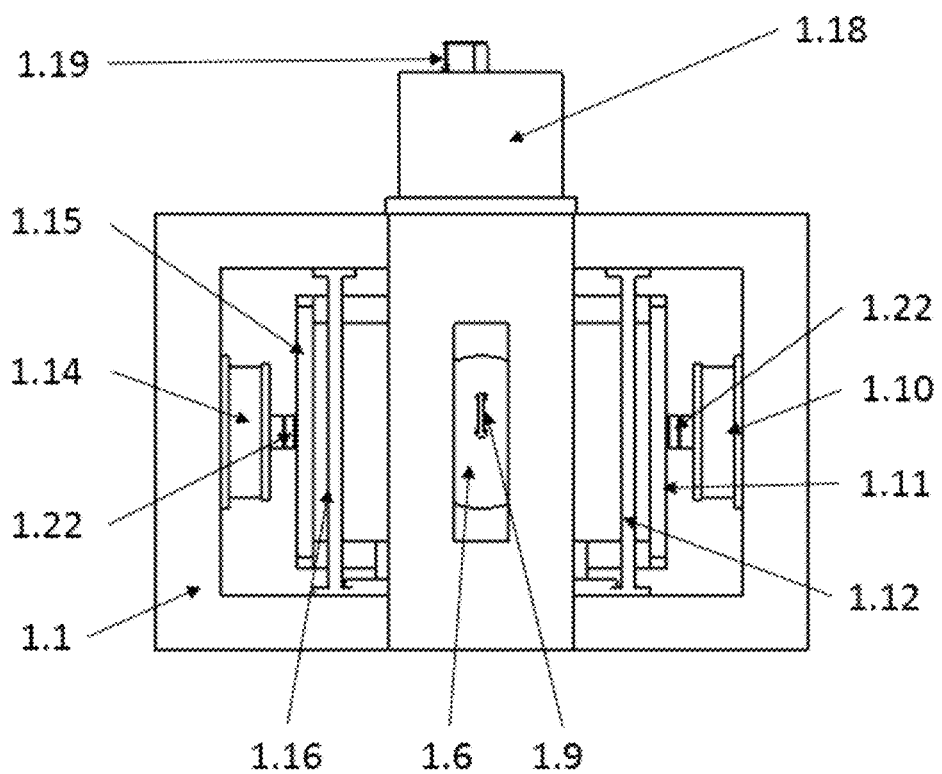
FIG. 7 is a front view of the true-triaxial loading system of the rock true-triaxial testing system based on CT scanning according to the present disclosure.
Figure 8:
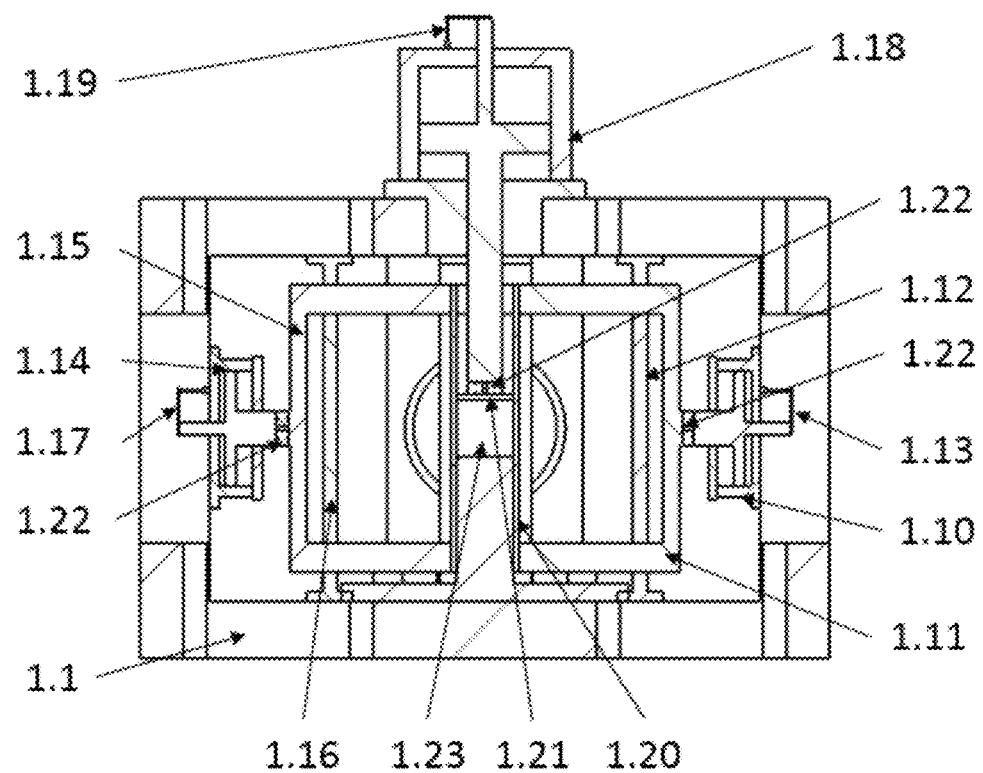
FIG. 8 is a left-right section view of the true-triaxial loading system of the rock true-triaxial testing system based on CT scanning according to the present disclosure.

Referring to FIGS. 1 to 10, a first embodiment of the present disclosure provides a rock true-triaxial testing system based on computerized tomography (CT) scanning. As shown in FIGS. 1, 2, and 8, the testing system includes true-triaxial loading system 1 and high-energy accelerator-based CT scanning system 2.

The true-triaxial loading system 1 is fixed to a ground and configured to apply a true-triaxial stress to cubic rock sample 1.23.

The high-energy accelerator-based CT scanning system 2 is located inside the true-triaxial loading system 1, and the high-energy accelerator-based CT scanning system 2 is configured to image an internal structure of the cubic rock sample 1.23 and rotate around the cubic rock sample 1.23.

Figure 9:
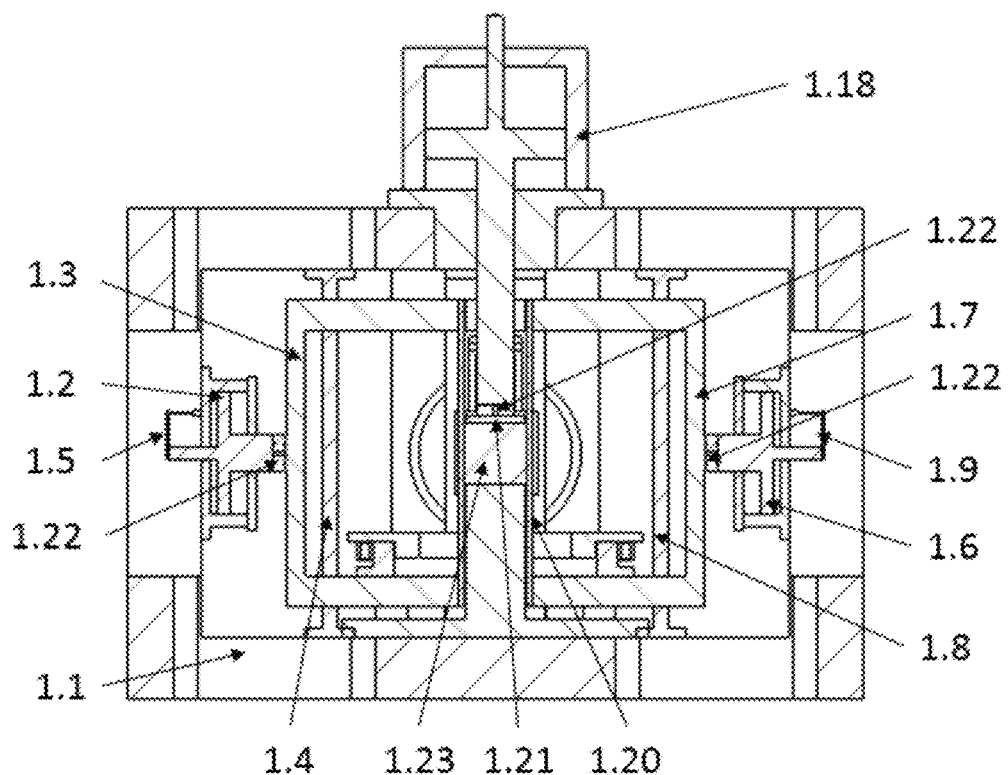
FIG. 9 is a front-back section view of the true-triaxial loading system of the rock true-triaxial testing system based on CT scanning according to the present disclosure.
Figure 10:
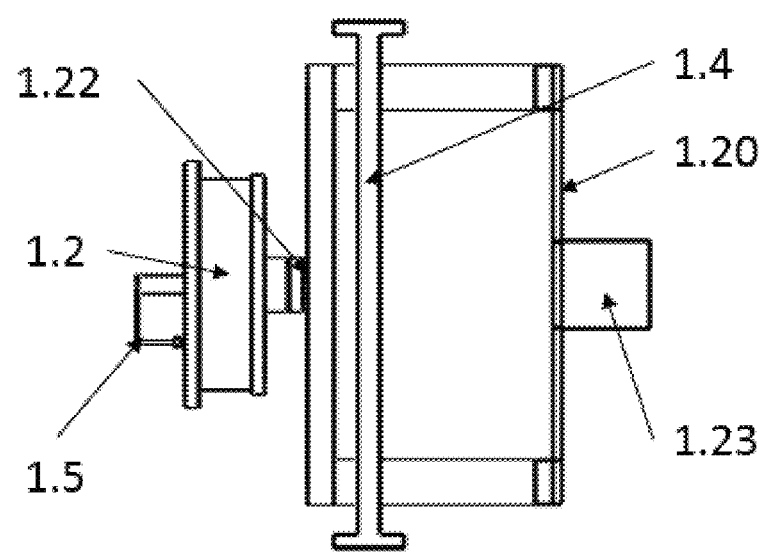
FIG. 10 is a back force loading and transfer diagram of the true-triaxial loading system of the rock true-triaxial testing system based on CT scanning according to the present disclosure.

Preferably, as shown in FIGS. 6, 9, and 10, the true-triaxial loading system 1 includes true-triaxial reaction frame 1.1, first loading pads 1.20, pressure sensors 1.22, the cubic rock sample 1.23, a first-axis loading system, a second-axis loading system, and a third-axis loading system.

The first-axis loading system includes first loading cylinders 1.2, first piston extension rods 1.3, first piston guide frames 1.4, and first displacement sensors 1.5.

The true-triaxial reaction frame 1.1 is fixed to the ground and the first loading cylinder 1.2. A piston rod of the first loading cylinder 1.2 is fixed to one end of the pressure sensor 1.22, and the other end of the pressure sensor 1.22 is fixed to the first piston extension rod 1.3. The first piston extension rod 1.3 passes through the high-energy accelerator-based CT scanning system 2 and is fixed to the first loading pad 1.20. The first loading pad 1.20 is configured to squeeze the cubic rock sample 1.23. The cubic rock sample 1.23 is connected to the high-energy accelerator-based CT scanning system 2. The first piston extension rod 1.3 is located inside the first piston guide frame 1.4, and the first piston guide frame 1.4 is fixed to the true-triaxial reaction frame 1.1.

The first displacement sensor 1.5 is fixed to the first loading cylinder 1.2 and configured to measure a displacement distance of the first piston extension rod 1.3.

Two first loading cylinders 1.2, two first piston extension rods 1.3, two first piston guide frames 1.4, two first displacement sensors 1.5, two first loading pads 1.20, and two pressure sensors 1.22 are symmetrically arranged along a center line of the true-triaxial reaction frame 1.1.

The second-axis loading system and the third-axis loading system are fixed to the true-triaxial reaction frame 1.1.

Two second loading cylinders 1.10, two second piston extension rods 1.11, two second piston guide frames 1.12, two second displacement sensors 1.13, two first loading pads 1.20, and two pressure sensors 1.22 are symmetrically arranged along the center line of the true-triaxial reaction frame 1.1. Specifically:

The first-axis loading system further includes fourth loading cylinder 1.6, fourth piston extension rod 1.7, fourth piston guide frame 1.8, and fourth displacement sensor 1.9.

The true-triaxial reaction frame 1.1 is fixed to the fourth loading cylinder 1.6. A piston rod of the fourth loading cylinder 1.6 is fixed to one end of the pressure sensor 1.22, and the other end of the pressure sensor 1.22 is fixed to the fourth piston extension rod 1.7. The fourth piston extension rod 1.7 passes through the high-energy accelerator-based CT scanning system 2 and is fixed to the first loading pad 1.20. The fourth piston extension rod 1.7 is located inside the fourth piston guide frame 1.8, and the fourth piston guide frame 1.8 is fixed to the true-triaxial reaction frame 1.1.

The fourth displacement sensor 1.9 is fixed to the fourth loading cylinder 1.6 and configured to measure a displacement distance of the fourth piston extension rod 1.7.

In the testing system, the first-axis loading system is a stress loading system in a front-to-back direction relative to a horizontal direction.

Preferably, as shown in FIGS. 6, 7, 8 and 9, the second-axis loading system includes second loading cylinders 1.10, second piston extension rods 1.11, second piston guide frames 1.12, and second displacement sensors 1.13.

The true-triaxial reaction frame 1.1 is fixed to the second loading cylinder 1.10. A piston rod of the second loading cylinder 1.10 is fixed to one end of the pressure sensor 1.22, and the other end of the pressure sensor 1.22 is fixed to the second piston extension rod 1.11. The second piston extension rod 1.11 passes through the high-energy accelerator-based CT scanning system 2 and is fixed to the first loading pad 1.20. The first loading pad 1.20 is configured to squeeze the cubic rock sample 1.23. The second piston extension rod 1.11 is located inside the second piston guide frame 1.12, and the second piston guide frame 1.12 is fixed to the true-triaxial reaction frame 1.1.

The second displacement sensor 1.13 is fixed to the second loading cylinder 1.10 and configured to measure a displacement distance of the second piston extension rod 1.11.

Two second loading cylinders 1.10, two second piston extension rods 1.11, two second piston guide frames 1.12, two second displacement sensors 1.13, two first loading pads 1.20, and two pressure sensors 1.22 are symmetrically arranged along the center line of the true-triaxial reaction frame 1.1.

Two second loading cylinders 1.10, two second piston extension rods 1.11, two second piston guide frames 1.12, two second displacement sensors 1.13, two first loading pads 1.20, and two pressure sensors 1.22 are symmetrically arranged along the center line of the true-triaxial reaction frame 1.1. Specifically:

The second-axis loading system further includes fifth loading cylinder 1.14, fifth piston extension rod 1.15, fifth piston guide frame 1.16, and fifth displacement sensor 1.17.

The true-triaxial reaction frame 1.1 is fixed to the fifth loading cylinder 1.14. A piston rod of the fifth loading cylinder 1.14 is fixed to one end of the pressure sensor 1.22, and the other end of the pressure sensor 1.22 is fixed to the fifth piston extension rod 1.15. The fifth piston extension rod 1.15 passes through the high-energy accelerator-based CT scanning system 2 and is fixed to the first loading pad 1.20. The fifth piston extension rod 1.15 is located inside the fifth piston guide frame 1.16, and the fifth piston guide frame 1.16 is fixed to the true-triaxial reaction frame 1.1.

The fifth displacement sensor 1.17 is fixed to the fifth loading cylinder 1.14 and configured to measure a displacement distance of the fifth piston extension rod 1.15.

The first piston extension rod 1.3, the second piston extension rod 1.11, the fourth piston extension rod 1.7, and the fifth piston extension rod 1.15 are provided to keep the above device out of a field of view of a CT scan, so as to reduce radiation attenuation and ensure imaging quality.

The first piston guide frame 1.4, the second piston guide frame 1.12, the fourth piston guide frame 1.8, and the fifth piston guide frame 1.16 are provided to limit the shaking of the corresponding piston extension rod and ensure a stable and smooth loading process.

In the testing system, the second-axis loading system is a stress loading system in a left-to-right direction relative to the horizontal direction.

In this embodiment, the loading pads fixed to the plurality of piston extension rods are all first loading pads 1.20, and the sensors fixed to the piston rods of the plurality of loading cylinders are all pressure sensors 1.22.

Preferably, as shown in FIGS. 6, 7, and 8, the third-axis loading system includes third loading cylinder 1.18, third displacement sensor 1.19, and second loading pad 1.21.

The true-triaxial reaction frame 1.1 is fixed to the third loading cylinder 1.18. A piston rod of the third loading cylinder 1.18 is fixed to one end of the pressure sensor 1.22, and the other end of the pressure sensor 1.22 is fixed to the second loading pad 1.21. The second loading pad 1.21 is configured to squeeze the cubic rock sample 1.23.

The third displacement sensor 1.19 is fixed to the third loading cylinder 1.18 and configured to measure a displacement distance of the second loading pad 1.21.

In the testing system, the third-axis loading system is configured to apply a stress from top to bottom in a vertical direction.

Figure 3:
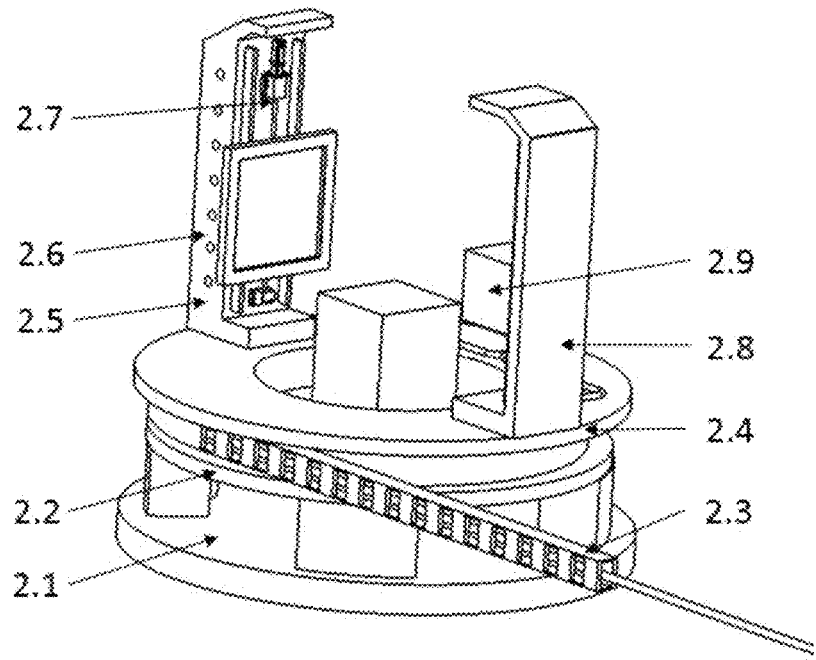
FIG. 3 is an isometric diagram of a high-energy accelerator-based CT scanning system of the rock true-triaxial testing system based on CT scanning according to the present disclosure.
Figure 4:
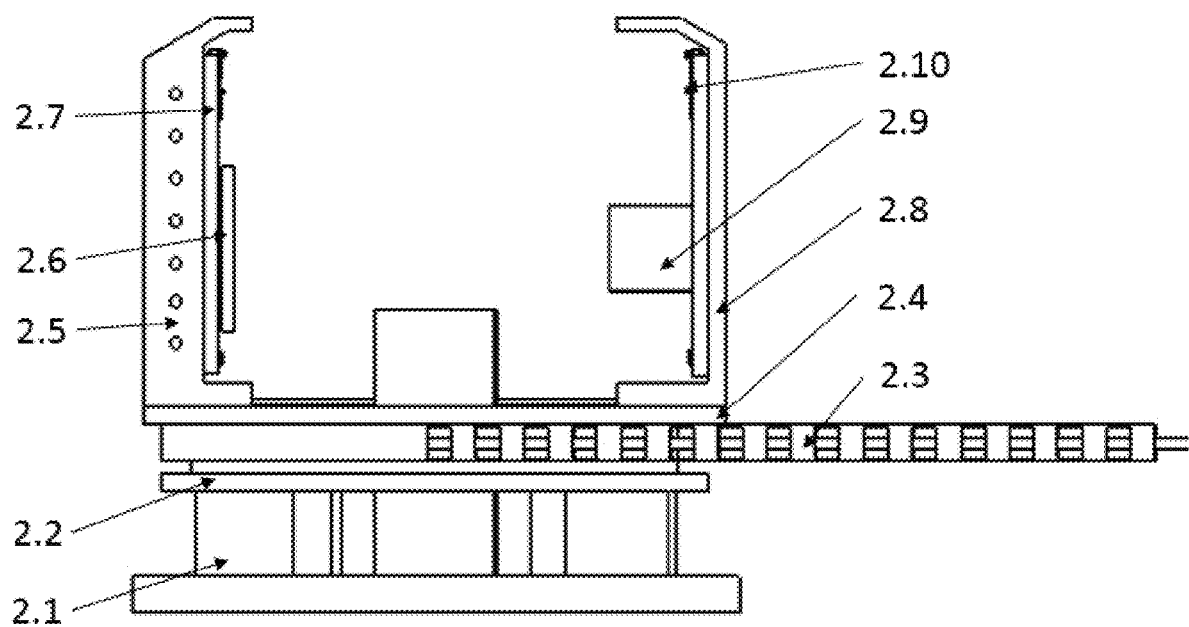
FIG. 4 is a front view of the high-energy accelerator-based CT scanning system of the rock true-triaxial testing system based on CT scanning according to the present disclosure.

Preferably, as shown in FIGS. 2, 3, and 4, the high-energy accelerator-based CT scanning system 2 includes high-energy accelerator-based CT support base 2.1, turntable stator 2.2, rotating tow 2.3, turntable rotor 2.4, detector bracket 2.5, detector 2.6, detector lifting system 2.7, radiation source bracket 2.8, radiation source 2.9, and radiation source lifting system 2.10.

A lower surface of the high-energy accelerator-based CT support base 2.1 is connected to the true-triaxial reaction frame 1.1, and an upper surface of the high-energy accelerator-based CT support base 2.1 is connected to the cubic rock sample 1.23 and the turntable stator 2.2. The turntable stator 2.2 is connected to the turntable rotor 2.4 through a bearing.

The turntable rotor 2.4 is fixed to the detector bracket 2.5. The detector bracket 2.5 is fixed to the detector lifting system 2.7. The detector lifting system 2.7 is fixed to the detector 2.6. The detector 2.6 is configured to image the internal structure of the cubic rock sample 1.23.

The turntable rotor 2.4 is fixed to the radiation source bracket 2.8. The radiation source bracket 2.8 is fixed to the radiation source lifting system 2.10. The radiation source lifting system 2.10 is fixed to the radiation source 2.9. The radiation source 2.9 is configured to emit an X-ray to the cubic rock sample 1.23.

The cubic rock sample 1.23 is connected to the high-energy accelerator-based CT support base 2.1. An end of the rotating tow 2.3 is fixed to the turntable rotor 2.4, and the rotating tow 2.3 is configured to coil around an outer circumference of the turntable stator 2.2. The rotating tow 2.3 is configured to pull a CT line of the high-energy accelerator-based CT scanning system 2.

The high-energy accelerator-based CT support base 2.1 is configured to support a turntable around a plurality of piston extension rods to avoid interference between the high-energy accelerator-based CT scanning system 2 and the plurality of piston extension rods during rotation, and to provide a supporting reaction force for the cubic rock sample 1.23. The turntable stator 2.2 and the turntable rotor 2.4 work together, thereby carrying the radiation source 2.9 and the detector 2.6 to rotate relative to the cubic rock sample 1.23 at 360°. The detector lifting system 2.7 and the radiation source lifting system 2.10 are configured to adjust a CT scan position such that the cubic rock sample 1.23 is within an optimal field of view of the CT scan. The radiation source 2.9 is configured to generate an X-ray. The detector 2.6 is configured to receive an attenuated ray and detect imaging. The rotating tow 2.3 is configured to coil the CT line so as to avoid a line entanglement problem caused by rotation.

Figure 5:
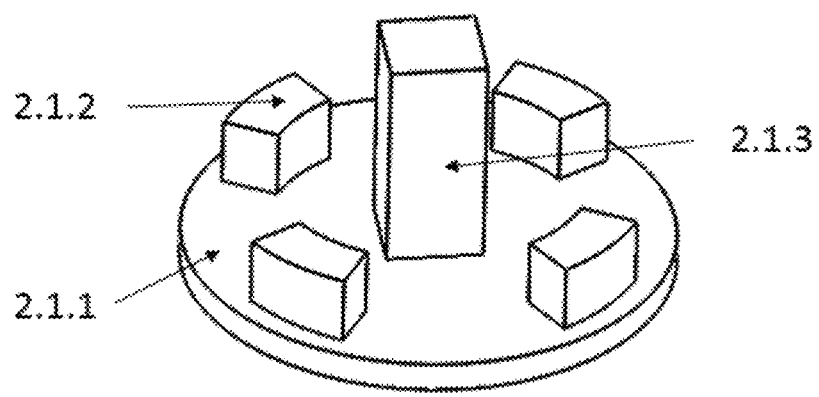
FIG. 5 is a schematic diagram of a high-energy accelerator-based CT support base of the rock true-triaxial testing system based on CT scanning according to the present disclosure.

Preferably, as shown in FIGS. 4 and 5, the high-energy accelerator-based CT support base 2.1 includes base connecting plate 2.1.1, CT support bosses 2.1.2, and lower reaction pad 2.1.3.

A lower surface of the base connecting plate 2.1.1 is fixed to the true-triaxial reaction frame 1.1, and an upper surface of the base connecting plate 2.1.1 is fixed to the plurality of CT support bosses 2.1.2. The plurality of CT support bosses 2.1.2 are fixed to the turntable stator 2.2.

The upper surface of the base connecting plate 2.1.1 is fixed to a lower surface of the lower reaction pad 2.1.3, and an upper surface of the lower reaction pad 2.1.3 is fixed to the cubic rock sample 1.23.

The plurality of CT support bosses 2.1.2 are evenly distributed along the upper surface of the base connecting plate 2.1.1 in a circumferential direction.

Preferably, as shown in FIGS. 1 and 2, the testing system further includes oil source power system 3. The oil source power system 3 is fixed to the ground and configured to provide a power source for the true-triaxial loading system 1.

Preferably, as shown in FIGS. 1 and 2, the testing system further includes comprehensive control system 4. The comprehensive control system 4 is fixed to the ground and configured to implement loading control and signal acquisition of the true-triaxial loading system 1, as well as control and acquisition of photoelectric and control signals of the high-energy accelerator-based CT scanning system 2.

Preferably, as shown in FIG. 5, the lower reaction pad 2.1.3 is configured to provide a supporting reaction force for the cubic rock sample 1.23.

Preferably, as shown in FIGS. 6, 8, and 9, the first loading pads 1.20 are made of titanium alloy or aviation aluminum alloy.

The first loading pad 1.20 can be made of high-strength and low-density alloy, such as titanium alloy and aviation aluminum alloy, which ensures rigidity and less radiation absorption.

As shown in FIGS. 1 to 10, a second embodiment of the present disclosure provides a rock true-triaxial testing method based on CT scanning, which is based on a rock true-triaxial testing system based on CT scanning and includes the following steps.

S1. First loading pad 1.20, second loading pad 1.21, and cubic rock sample 1.23 are removed from true-triaxial loading system 1.

S2. Radiation source 2.9 and detector 2.6 are adjusted and aligned without any object obstructing between the radiation source and the detector. High-energy accelerator-based CT scanning system 2 is turned on to perform a background scan.

S3. After the background scan is completed, the cubic rock sample 1.23 is assembled in the first loading pad 1.20 and then placed in the true-triaxial loading system 1.

S4. Connection of a sensor line and lower reaction pad 2.1.3 is checked.

S5. If there are no errors, a first-axis loading system and a second-axis loading system are started, and a horizontal stress over time reaches a target value for a test.

S6. The high-energy accelerator-based CT scanning system 2 is started to perform initial-stage scanning of the cubic rock sample 1.23 under true-triaxial loading.

S7. A third-axis loading system is started to continuously load the cubic rock sample 1.23, and a stress-strain curve is recorded.

S8. When a stress loaded by the third-axis loading system reaches a certain target value, the loading is stopped, and the stress is maintained. Then the high-energy accelerator-based CT scanning system 2 is started again to perform second-stage scanning of the cubic rock sample 1.23 under true-triaxial loading.

S9. The operation proceeds to the step S7, and the steps S7 and S8 are repeated. The scanning is performed during a plurality of loading stages according to a testing program until the rock is finally destroyed by loading.

S10. The third-axis loading system is unloaded till a 0 stress, and then the horizontal stress of the first-axis loading system and the second-axis loading system is unloaded.

S11. The cubic rock sample 1.23 is removed, test data are organized, and a photo is taken to describe the damaged cube rock sample 1.23.

S12. The test is over.

These steps are described in order in the above embodiments. However, those skilled in the art may understand that, in order to achieve the effects of these embodiments, different steps may not be necessarily executed in such an order, but may be executed simultaneously (in parallel) or in a reversed order. These simple changes should fall within the protection scope of the present disclosure.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

The invention claimed is:

1. A rock true-triaxial testing system based on computerized tomography (CT) scanning, comprising a true-triaxial loading system and a high-energy accelerator-based CT scanning system, wherein
the true-triaxial loading system is fixed to a ground and configured to apply a true-triaxial stress to a cubic rock sample;
the high-energy accelerator-based CT scanning system is located inside the true-triaxial loading system, and the high-energy accelerator-based CT scanning system is configured to image an internal structure of the cubic rock sample and rotate around the cubic rock sample;
the true-triaxial loading system comprises a true-triaxial reaction frame, first loading pads, pressure sensors, the cubic rock sample, a first-axis loading system, a second-axis loading system, and a third-axis loading system;
the first-axis loading system comprises first loading cylinders, first piston extension rods, first piston guide frames, and first displacement sensors;
the true-triaxial reaction frame is fixed to the ground and the first loading cylinder; a piston rod of the first loading cylinder is fixed to a first end of a first pressure sensor of the pressure sensors, and a second end of the first pressure sensor is fixed to the first piston extension rod; the first piston extension rod passes through the high-energy accelerator-based CT scanning system and is fixed to the first loading pad; the first loading pad is configured to squeeze the cubic rock sample; the cubic rock sample is connected to the high-energy accelerator-based CT scanning system; the first piston extension rod is located inside the first piston guide frame; and the first piston guide frame is fixed to the true-triaxial reaction frame;

the first displacement sensor is fixed to the first loading cylinder and configured to measure a displacement distance of the first piston extension rod;

two first loading cylinders, two first piston extension rods, two first piston guide frames, two first displacement sensors, two first loading pads, and two first pressure sensors are symmetrically arranged along a center line of the true-triaxial reaction frame;

the second-axis loading system and the third-axis loading system are fixed to the true-triaxial reaction frame;

the second-axis loading system comprises second loading cylinders, second piston extension rods, second piston guide frames, and second displacement sensors;

the true-triaxial reaction frame is fixed to the second loading cylinder; a piston rod of the second loading cylinder is fixed to a first end of a second pressure sensor of the pressure sensors, and a second end of the second pressure sensor is fixed to the second piston extension rod; the second piston extension rod passes through the high-energy accelerator-based CT scanning system and is fixed to the first loading pad; the first loading pad is configured to squeeze the cubic rock sample; the second piston extension rod is located inside the second piston guide frame; and the second piston guide frame is fixed to the true-triaxial reaction frame;

the second displacement sensor is fixed to the second loading cylinder and configured to measure a displacement distance of the second piston extension rod;

two second loading cylinders, two second piston extension rods, two second piston guide frames, two second displacement sensors, two first loading pads, and two second pressure sensors are symmetrically arranged along the center line of the true-triaxial reaction frame;

the third-axis loading system comprises a third loading cylinder, a third displacement sensor, and a second loading pad;

the true-triaxial reaction frame is fixed to the third loading cylinder; a piston rod of the third loading cylinder is fixed to a first end of a third pressure sensor of the pressure sensors, and a second end of the third pressure sensor is fixed to the second loading pad; and the second loading pad is configured to squeeze the cubic rock sample;

the third displacement sensor is fixed to the third loading cylinder and configured to measure a displacement distance of the second loading pad;

the high-energy accelerator-based CT scanning system comprises a high-energy accelerator-based CT support base, a turntable stator, a rotating tow, a turntable rotor, a detector bracket, a detector, a detector lifting system, a radiation source bracket, a radiation source, and a radiation source lifting system;

a lower surface of the high-energy accelerator-based CT support base is connected to the true-triaxial reaction frame, and an upper surface of the high-energy accelerator-based CT support base is connected to the cubic rock sample and the turntable stator; and the turntable stator is connected to the turntable rotor through a bearing;

the turntable rotor is fixed to the detector bracket; the detector bracket is fixed to the detector lifting system; the detector lifting system is fixed to the detector; and the detector is configured to image the internal structure of the cubic rock sample;

the turntable rotor is fixed to the radiation source bracket; the radiation source bracket is fixed to the radiation source lifting system; the radiation source lifting system is fixed to the radiation source; and the radiation source is configured to emit an X-ray to the cubic rock sample; and an end of the rotating tow is fixed to the turntable rotor, and the rotating tow is configured to coil around an outer circumference of the turntable stator; and the rotating tow is configured to pull a CT line of the high-energy accelerator-based CT scanning system.

2. The rock true-triaxial testing system based on CT scanning according to claim 1, wherein the high-energy accelerator-based CT support base comprises a base connecting plate, a plurality of CT support bosses, and a lower reaction pad;

a lower surface of the base connecting plate is fixed to the true-triaxial reaction frame, and an upper surface of the base connecting plate is fixed to the plurality of CT support bosses; and the plurality of CT support bosses are fixed to the turntable stator; and the upper surface of the base connecting plate is fixed to a lower surface of the lower reaction pad, and an upper surface of the lower reaction pad is fixed to the cubic rock sample.

3. The rock true-triaxial testing system based on CT scanning according to claim 2, further comprising an oil source power system; wherein the oil source power system is fixed to the ground and configured to provide a power source for the true-triaxial loading system.

4. The rock true-triaxial testing system based on CT scanning according to claim 3, further comprising a comprehensive control system; wherein the comprehensive control system is fixed to the ground and configured to implement loading control and signal acquisition of the true-triaxial loading system and implement control and acquisition of photoelectric and control signals of the high-energy accelerator-based CT scanning system.

5. The rock true-triaxial testing system based on CT scanning according to claim 4, wherein the lower reaction pad is configured to provide a supporting reaction force for the cubic rock sample.

6. The rock true-triaxial testing system based on CT scanning according to claim 5, wherein the first loading pads are made of titanium alloy or aviation aluminum alloy.

* * * * *